United States Patent [19]

Heath et al.

[11] Patent Number: 4,770,787
[45] Date of Patent: Sep. 13, 1988

[54] METHOD OF OPERATING A FLUID FLOW TRANSFER DEVICE

[75] Inventors: Gary B. Heath, Aurora; William G. Palsulich, Boulder; Keith J. Manica, Littleton; Jack C. Swan, Jr., Boulder, all of Colo.

[73] Assignee: Cobe Laboratories, Inc., Lakewood, Colo.

[21] Appl. No.: 13,355

[22] Filed: Feb. 11, 1987

Related U.S. Application Data

[62] Division of Ser. No. 748,545, Jun. 25, 1985, Pat. No. 4,666,598.

[51] Int. Cl.⁴ .............................................. B01D 13/00
[52] U.S. Cl. ........................................ 210/646; 604/4; 210/741; 210/764
[58] Field of Search ................. 210/90, 137, 206, 239, 210/232, 321.2, 321.3, 321.4, 416.1, 433.2, 645, 646, 741, 764, 321.72, 321.74, 321.75, 321.78, 321.79, 321.8, 321.81; 604/4

[56] References Cited

U.S. PATENT DOCUMENTS

| | | | |
|---|---|---|---|
| 3,774,762 | 11/1973 | Lichtenstein | 210/321.3 X |
| 4,263,808 | 4/1981 | Bellotti et al. | 210/321.1 X |
| 4,293,413 | 10/1981 | Schnell | 210/321.3 X |
| 4,370,983 | 2/1983 | Lichtenstein | 210/321.2 X |
| 4,666,598 | 5/1987 | Heath et al. | 210/416.1 X |

FOREIGN PATENT DOCUMENTS 0134436 3/1985 European Pat. Off. .

Primary Examiner—Richard V. Fisher
Assistant Examiner—W. Gary Jones

[57] ABSTRACT

A fluid flow chamber cassette that can be mounted with either its front wall or rear wall against a supporting machine and has a flexible tube that extends from a sidewall and forms a loop that is symmetrical about a loop axis that is transverse to the side wall so that the loop will be acted upon by a pump roller on the machine both when the front wall is against the machine and when the rear wall is against the machine. Also disclosed is automatically fixing the initial liquid levels and amounts of air in venous and arterial chambers of fluid flow transfer device apparatus by having the arterial chamber inlet enter the arterial chamber at a position higher than the arterial chamber outlet, having the venous chamber inlet enter the venous chamber at a position higher than the venous chamber outlet, and priming the apparatus by causing reverse flow, so that the liquid rises in the venous and arterial chambers to the level of the entrances of the inlets. Also disclosed is sensing pressure of fluid in a fluid flow chamber by placing an impermeable flexible diaphragm over a hole in a rigid wall of the fluid flow chamber, providing a second chamber on the other side of the diaphragm, and sensing the pressure in the second chamber.

4 Claims, 2 Drawing Sheets

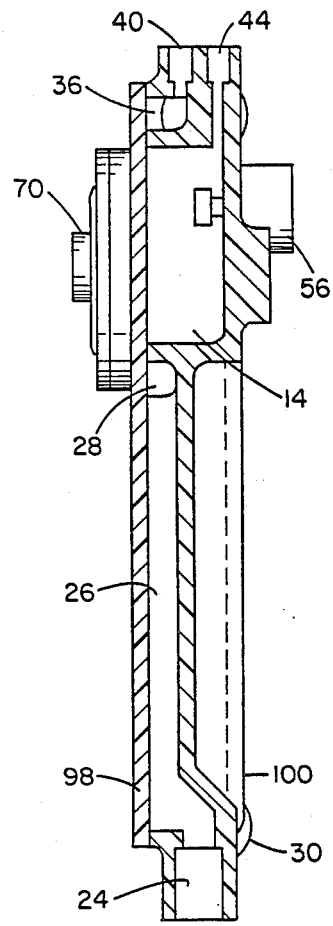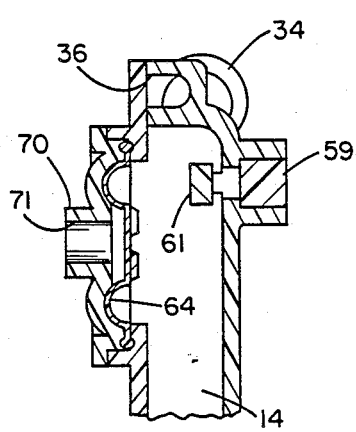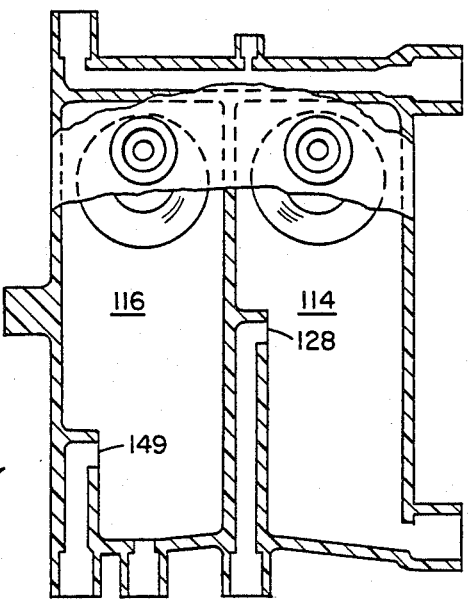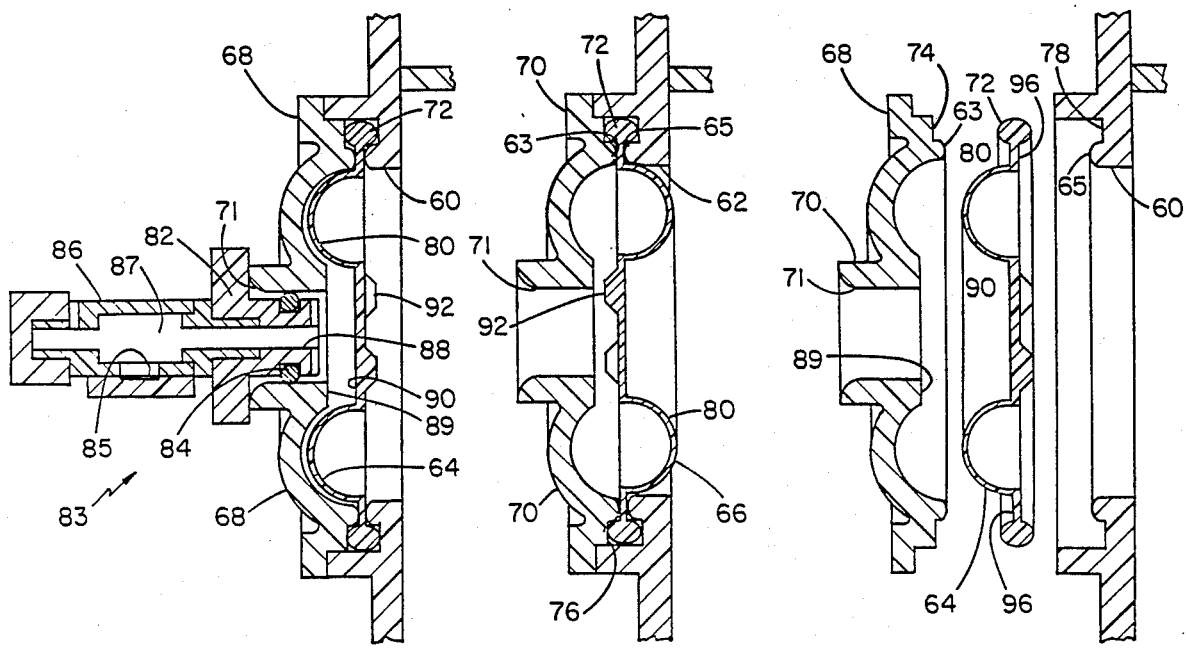

METHOD OF OPERATING A FLUID FLOW TRANSFER DEVICE

This application is a division, of application Ser. No. 748,545, filed June 25, 1985 now U.S. Pat. No. 4,666,598.

FIELD OF THE INVENTION

The invention relates to apparatus used with fluid flow transfer devices such as dialyzers and methods of using the apparatus.

BACKGROUND OF THE INVENTION

Fluid flow transfer devices such as dialyzers are used to continuously remove impurities from a patient's blood. The blood is typically pumped through tubes and arterial and venous bubble traps of disposable tubing sets connecting the patient to a dialyzer mounted on a dialysate preparation and supply machine.

Bellotti et al. U.S. Pat. No. 4,263,808 discloses, as a tubing set replacement, a one-piece hydraulic circuit that includes arterial and venous bubble trap chambers in which blood enters at entrances above the bottoms of the chambers and leaves near the bottoms of the chambers. Pressure in the chambers can be determined by transducers placed against impermeable latex membranes covering holes communicating with upper portions of the chambers.

SUMMARY OF THE INVENTION

In one aspect the invention features a fluid flow chamber cassette that can be mounted with either its front wall or rear wall against a supporting machine and has a flexible tube that extends from a sidewall and forms a loop that is symmetrical about a loop axis that is transverse to the side wall so that the loop will be acted upon by a pump roller on the machine both when the front wall is against the machine and when the rear wall is against the machine. The orientation of the cassette and the direction of fluid flow through the cassette can thus be changed by simply changing whether the front or the rear wall is mounted against the machine.

In preferred embodiments the flexible tube is connected at one end to a chamber outlet at the bottom of the chamber and at the other end to the inlet of a flow passage in the cassette, which inlet is located at the same distance from the loop axis as the chamber outlet; the cassette has two chambers (arterial and venous chambers) and additional flexible tubes for connecting a dialyzer between the flow passage and the venous chamber; the outlet of the venous chamber is at the bottom of the venous chamber; and the inlets to the arterial and venous chambers enter the arterial and venous chambers at locations above the outlets of the chambers. In use with a dialyzer, blood from a patient flows through the arterial chamber, the symmetrical pump loop, and the flow passage to the dialyzer, and from there through the venous chamber and back to the patient. After dialysis has been completed, the cassette and dialyzer are inverted and remounted on the machine in an upside down position, and disinfecting solution is pumped through them in the reverse direction, filling all regions of the cassette, dialyzer and tubing.

In another aspect the invention features automatically fixing the initial liquid levels and amounts of air in venous and arterial chambers of fluid flow transfer device apparatus by having the arterial chamber inlet enter the arterial chamber at a position higher than the arterial chamber outlet, having the venous chamber inlet enter the venous chamber at a position higher than the venous chamber outlet, and priming the apparatus by causing reverse flow, so that the liquid rises in the venous and arterial chambers to the levels of the entrances of the inlets, and the amount of air in the chambers remains fixed, even after flow is reversed during normal operation with blood.

In another aspect the invention features sensing pressure of fluid in a fluid flow chamber by placing an impermeable flexible diaphragm over a hole in a rigid wall of the fluid flow chamber, providing a second chamber on the other side of the diaphragm, and sensing the pressure in the second chamber.

In preferred embodiments the diaphragm is circular and includes a corrugated portion formed symmetrically about the center, so that the diaphragm moves with little stretching, and the diaphragm is sufficiently elastomeric so that it returns to its original shape when not restrained from movement; the corrugated portion is semicircular in cross-section; and the fluid flow chamber is provided by a cassette that is removably mounted on a machine carrying a pressure transducer, and the second chamber is defined by a portion of the machine surrounding the transducer and a rigid retainer that covers the diaphragm, is carried by the cassette and has an opening adapted to sealably engage the portion surrounding the transducer on the machine.

Other features and advantages of the invention will be apparent from the following detailed description of a preferred embodiment of the invention and from the claims.

DESCRIPTION OF THE PREFERRED EMBODIMENT

The drawings will be briefly described first.

DRAWINGS

FIG. 4 is a vertical sectional view, taken at 4—4 of FIG. 1, of the FIG. 1 cassette.

FIG. 5 is a partial vertical sectional view, taken at 5—5 of FIG. 1, of the FIG. 1 cassette.

FIG. 6 is a partial vertical sectional view, taken at 6—6 of FIG. 1, showing a pressure sensing portion of the FIG. 1 cassette connected to a pressure sensor of a machine on which the FIG. 1 cassette is mounted.

FIG. 7 is a partial sectional view, taken at 7—7 of FIG. 1, showing another pressure sensing portion of the FIG. 1 cassette.

FIG. 8 is an exploded partial sectional view of the FIG. 6 pressure sensing portion.

FIG. 9 is an elevation, partially in section, of another embodiment of a cassette according to the invention.

STRUCTURE

Figure 1:
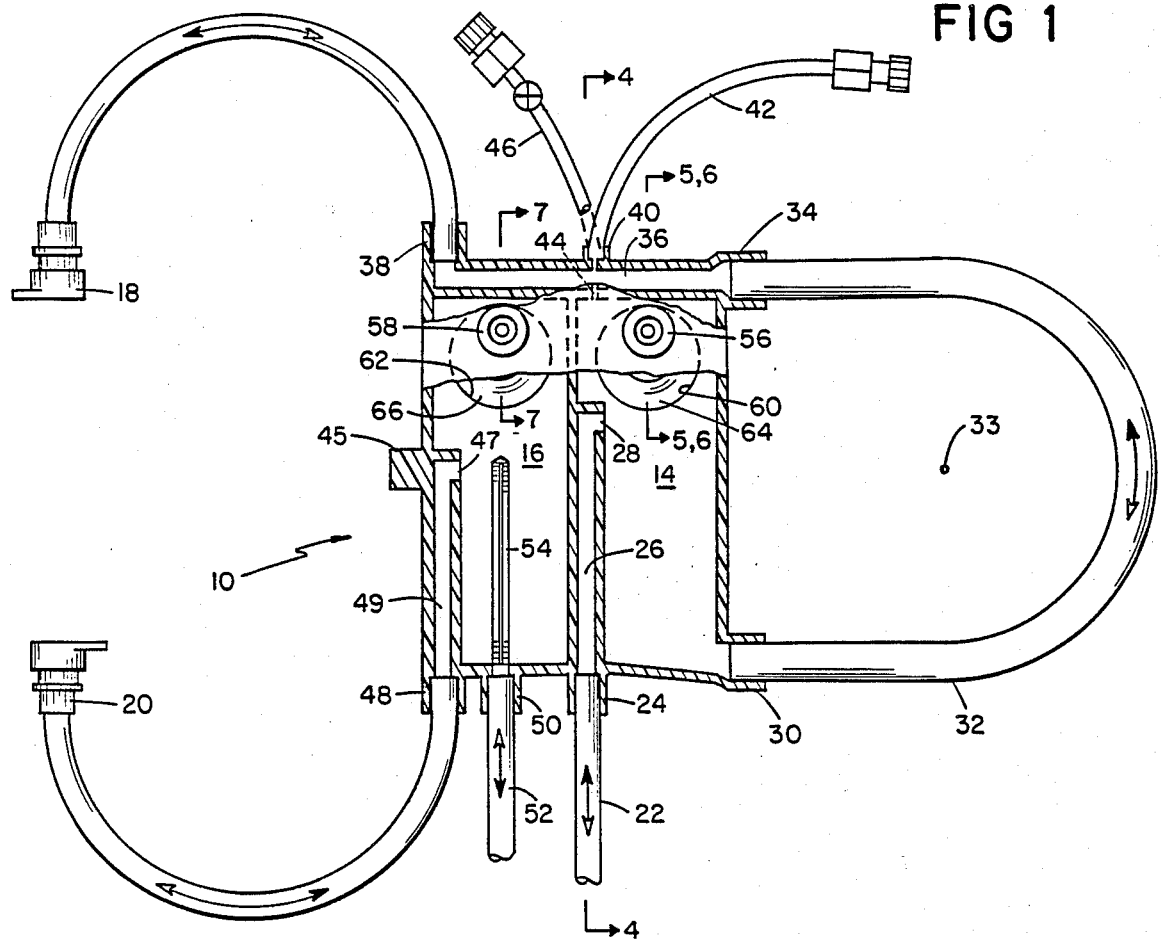
FIG. 1 is a diagrammatic elevation, partially in section, of a cassette for use with a fluid flow transfer device according to the invention.
Figures 2, 3:
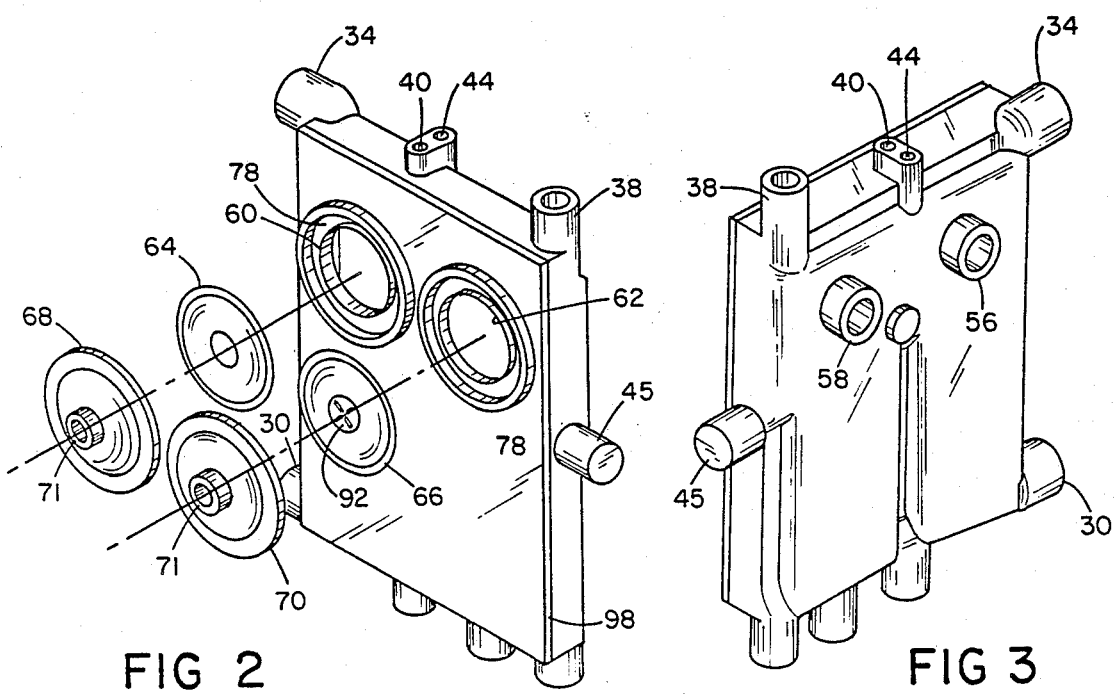
FIG. 2 is a diagrammatic, partially exploded, rear perspective view of the FIG. 1 cassette.
FIG. 3 is a front perspective view of the FIG. 1 cassette.

Referring to FIGS. 1-5, there is shown fluid flow chamber cassette 10, including tubing for connection to access needles for a patient, a blood pump roller, a dialyzer, and sources of saline and heparin solutions. Cassette 10 is made of clear PVC plastic and includes two major fluid flow chambers, arterial chamber 14 and venous chamber 16, through which blood flows prior to and after passing through a dialyzer connected to dialyzer inflow tube 18 and dialyzer outflow tube 20.

Arterial tube 22 is connected to arterial inlet 24, leading to narrow vertical inflow passage 26 that enters arterial chamber 14 about two-thirds of the way up chamber 14 at opening 28. At the bottom of arterial chamber 14 is arterial outlet 30 connected to flexible tube 32, that forms a loop that is symmetrical about axis 33 and is squeezed by the rollers of a peristaltic pump on a dialysate preparation machine (not shown) on which cassette 10 is mounted in use.

The other end of tube 32 is connected to inlet 34 to channel 36, which extends along the upper portion of cassette 10 and ends at outlet 38, connected to dialyzer inflow tube 18. Heparin port 40 at the top of cassette 10 is connected to heparin tube 42 and leads to channel 36. Saline inflow port 44 is connected to saline tube 46 and leads to the upper part of arterial chamber 14 (FIG. 4).

Dialyzer tube 20 is connected to inlet 48 leading to narrow vertical inflow passage 49 that enters venous chamber 16 about slightly more than one-half of the way up chamber 16 at opening 47. Outlet 50 of venous chamber 16 is connected to venous tube 52. Positioned above and blocking the entrance to outlet 50 is plastic blood filter 54. On the front walls of arterial chamber 14 and venous chamber 16 are access ports 56, 58, which have rubber plugs 59 sealing them shut (FIG. 5). Needle guards 61 prevent needles inserted into plugs 59 from going too far into chambers 14, 16.

Referring to FIGS. 2 and 6-8, is seen that back plate 98 has holes 60, 62 to arterial chamber 14 and venous chamber 16 covered by diaphragms 64, 66, which are identical, except that their orientations are reversed. Diaphragm 64, subject to negative pressure in arterial chamber 14, has its semicircular corrugated portion 80 extending away from chamber 14, and diaphragm 66, subjected to positive pressure in chamber 16 has its semicircular corrugated portion extending into chamber 16. Behind diaphragms 64, 66 are diaphragm retainers 68, 70, having cylindrical passages 71 therethrough for receiving cylindrical extensions 82 of pressure sensors 83 mounted on the face of the machine that cassette 10 is connected to in use (FIG. 6). At the peripheries of diaphragms 64, 66 are beads 72 that are squeezed between annular surfaces 74, 76 of retainers 68, 70 and opposing annular surfaces 78 surrounding holes 60, 62. Edge portions 96 of diaphragms 64, 66, are squeezed between lips 63 of retainers 68, 70 and opposing lips 65 surrounding holes 60, 62, thereby forming seals between the diaphragms and the retainers and between the diaphragms and the back plate.

Referring to FIG. 6, it is seen that extension 82 carries O-ring 84, which forms a seal with the inner surface of cylindrical passage 71. Pressure transducer element 85 is exposed to chamber 87, which includes the volume within walls 86, passage 88 (in extension 82) and the region between the inner surface of retainer 68 and diaphragm 64. An identical pressure sensor mates with the inner surface of cylindrical passage 71 of retainer 70. Semicircular corrugated portion 80 extends around diaphragm 64, is 0.125" in radius at its outer surface and extends 180° about its center. The opposing surface of retainer 68 has the same radius, but does not extend a full 180° near the center but ends at surface 89, located 0.065" above center portion 90 of diaphragm 64. On the opposite surface of diaphragms 64, 66 are four radial projections 92, useful on diaphragm 66 in the venous chamber to prevent blocking of passage 88. Diaphragm 64 is 0.010" thick at semicircular portion 80, and is 0.020" thick at center portion 90 and edge portion 96 near bead 72. Diaphragm 64 is made of silicone rubber (available under the trade designation MDX4-4515 from Dow Corning) and is nontoxic. Corrugated portion 80 can roll in either direction without stretch or friction, and is sufficiently elastomeric to return to its original shape when not restrained from movement by fluid conditions in the chambers.

As is perhaps best seen in FIG. 4, cassette 10 is primarily made of two molded PVC pieces, flat back plate 98, and front piece 100, in which are formed the ports and walls for the various chambers and passages. Back plate 98 is joined front piece 100 by solvent bonding. Retainers 6 similarly solvent bonded to back plate 98.

OPERATION

In use, cassette 10 is snapped onto the dialysate preparation machine (not shown) by clothespin-like clips on the machine that engage projection 45 and the tubular extensions providing arterial outlet 30 and flow passage inlet 34. After back plate 98 of cassette 10 has been brought against the machine and locked into position, extensions 82 of the pressure sensors on the machine are automatically inserted into cylindrical passages 71 of retainers 68, 70, sealing with them at O-rings 84. Looped tube 32 fits around the rollers of a peristaltic pump (not shown) also carried on the front of the machine; the axis of the blood pump intersects loop axis 33.

Referring to FIG. 1, the direction of flow during dialysis is shown by the solid arrowheads, and the direction of flow during priming is shown by the open arrowheads. Prior to use with a patient, cassette 10, its various tubes and the hollow fiber dialyzer connected to them are primed with saline solution by connecting the end of venous tube 52 to a saline bag and operating the pump acting on tube 32 in the direction indicated by the open arrowhead (clockwise direction). This causes the saline solution to be pulled into venous chamber 16. The amount of liquid in chamber 16 is automatically determined by the height of opening 47 at the end of inlet passage 49 from inlet 48. Once the saline solution reaches the level of opening 47, the fluid volume and the amount of air in chamber 16 does not change, except that the pump is operated at a slightly higher than normal speed when initially filling the venous chamber to provide a level slightly higher than opening 47 so that bubbles do not continue to be carried to the dialyzer during priming. Saline solution then travels through tube 20, the dialyzer connected to it, tube 18, passage 36 and tube 32 into the outlet to arterial chamber 14. The fluid level in arterial chamber 14 is automatically set by the height of opening 28. The saline solution then travels through arterial line 22. Once all the air has been removed from the dialyzer, the arterial line is connected to a needle which had been inserted into the patient and clamped shut. The dialyzer need not be inverted after priming, as was common in the prior practice. Also, because of the self-leveling of liquid in chambers 14, 16, the priming of the apparatus is much quicker than, requires less operator effort than, and is more reliable than the timing-consuming priming of prior blood tubing sets, which priming included manual liquid level adjustments.

A heparine source is connected to line 42, and a saline source is connected to line 46. Heparin is automatically fed into passage 36, to prevent blood clotting in the dialyzer. Because passage 36 is at positive pressure, the heparin will not be drawn into the apparatus at a faster than desired rate. Saline line 46 is maintained in a clamped position and is provided as an emergency supply of additional liquid to be quickly administered to the patient in case of shock.

Blood pump is then operated in the forward (counterclockwise) direction, drawing blood from the patient into tube 22 and through the passages of cassette 10 and the associated tubes, replacing the saline solution in it by forcing the saline solution out of the end of tube 52. Once cassette 10, the dialyzer, and associated tubes have filled with blood, the blood pump is stopped. The end of venous line 52 is connected to a needle into the patient, and dialysis can then begin with the pump going in the counterclockwise direction, the blood flowing as indicated by the solid arrowheads.

During dialysis the amounts of air within chambers 14, 16 remain constant. Pressure is monitored by pressure sensors 83, which are isolated from the blood flow path by nontoxic diaphragms 64, 66. Chamber 14 is generally at a negative pressure (about −150 mm Hg), and chamber 16 is generally at a positive pressure (about +150 mm Hg). The air spaces in chambers 14, 16 provide compliant volumes to accommodate pressure perturbations caused by the operation of the peristaltic pump. The level in arterial chamber 14 is slightly lower than it was during priming, and the level in venous chamber 16 is slightly higher than during priming, owing to the switching between positive and negative pressure conditions with the change in pump direction. Diaphragm 64 moves without stretch or friction (owing to corrugated portion 80) into chamber 14, causing the pressure in chamber 87 to be equal to that in chamber 14. Diaphragm 66 similarly moves toward retainer 70, rolling at corrugated portion 80 without stretch or friction, causing the pressure chamber associated with its transducer to equal that in chamber 16.

After dialysis, line 22 is disconnected from the patient and connected to a source of saline solution, allowing the blood in the hydraulic circuit to be returned to the patient. Heparine line 42 and saline line 46 are disconnected from the respective sources and reconnected together. Cassette 10 and the associated dialyzer are then inverted, with the front of cassette 10 being against the machine, and outlet 30 being at the top and inlet 34 being at the bottom. Disinfecting solution is then drawn into tube 22 and through the system by running the pump in a clockwise direction, causing the solution to occupy all regions in the circuit. Arterial line 22 and venous line 52 are connected together, and the cassette and dialyzer can then be stored with the solution, which will be flushed out prior to reuse on the same patient.

OTHER EMBODIMENTS

Other embodiments of the invention are within the scope of the following claims.

For example, FIG. 9 shows cassette 110 for use in single needle dialysis. Inlets 149, 128 to venous and arterial chambers 116, 114 are at lower positions (inlet 149 being about one-fourth of the way up from the bottom and inlet 128 being about one-half of the way up from the bottom), to provide larger air volumes, to permit the liquid volumes to vary during the arterial and venous phases with smaller pressure changes.

What is claimed is:

1. A method of operating fluid flow transfer apparatus, said method comprising
    providing a fluid flow transfer device, an arterial chamber, and a venous chamber, an inlet of said fluid flow transfer device being connected to an outlet of said arterial chamber, an outlet of said fluid flow transfer device being lower than said inlet of said transfer device and being connected to an inlet to said venous chamber, said arterial chamber having an inlet entering said arterial chamber at a position higher than said arterial chamber outlet, said venous chamber inlet entering said venous chamber at a position higher than an outlet of said venous chamber, and
    priming a blood flow path of said apparatus by pumping sterile priming solution through said venous chamber, fluid flow transfer device and arterial chamber in the opposite direction from normal operation of said apparatus, namely into said outlet of said venous chamber, whereby said sterile solution rises in said venous chamber to the level of the entrance of said venous chamber inlet, flows upward through said fluid flow transfer device, removing air bubbles in it, and into said arterial chamber, rising in said arterial chamber to the level of the entrance of said arterial chamber inlet, whereby the initial liquid levels and amounts of air in said arterial and venous chambers are automatically fixed at predetermined levels and amounts.

2. The method of claim 1 further comprising connecting the inlet of said arterial chamber to a patient, pumping in the direction opposite to that during said priming until said sterile solution in said apparatus has been replaced by blood, connecting the outlet of said venous chamber to said patient and continuing pumping in the same direction to cause transfer in said device.

3. The method of claim 2 further comprising sensing the pressure in said arterial and venous chambers during said continuing pumping.

4. The method of claim 3 further comprising connecting said inlet of said arterial chamber to a sterile solution, pumping to return blood to said patient, disconnecting said patient, turning said device and arterial and venous chambers upside down, and pumping disinfecting solution through said venous chamber outlet and through all regions in the blood flow path of said apparatus.

* * * * *